United States Patent [19]

Bullard

[11] 4,086,919
[45] May 2, 1978

[54] LARYNGOSCOPE

[76] Inventor: James R. Bullard, 6 Sayle Rd., Charleston, S.C. 29401

[21] Appl. No.: 703,839

[22] Filed: Jul. 9, 1976

[51] Int. Cl.² .............................................. A61B 1/06
[52] U.S. Cl. .......................................... 128/11; 128/6
[58] Field of Search .............................. 128/6, 10–13, 128/15, 16, 351

[56] References Cited

U.S. PATENT DOCUMENTS

| 1,246,338 | 11/1917 | Smit | 128/16 |
|---|---|---|---|
| 1,613,373 | 1/1927 | Beck | 128/15 |
| 2,354,471 | 7/1944 | Macintosh | 128/10 |
| 3,195,536 | 7/1965 | Hovnanian et al. | 128/16 |
| 3,598,113 | 8/1971 | Moore | 128/11 |
| 3,643,654 | 2/1972 | Felbarg | 128/11 |
| 3,677,262 | 7/1972 | Zukowski | 128/6 |
| 3,766,909 | 10/1973 | Ozbey | 128/11 |
| 3,771,514 | 11/1973 | Huffman | 128/11 |
| 3,776,222 | 12/1973 | Smiddy | 128/11 |
| 3,884,222 | 5/1975 | Moore | 128/11 |
| 3,913,568 | 10/1975 | Carpenter | 128/11 |

*Primary Examiner*—Robert W. Michell
*Assistant Examiner*—Henry S. Layton
*Attorney, Agent, or Firm*—Luke J. Wilburn, Jr.; Wellington M. Manning, Jr.

[57] ABSTRACT

An improved laryngoscope for visualizing the glottis of the human body to facilitate endotracheal intubation comprising a thin, rigid blade construction of anatomically curved configuration to conform to the oral and pharyngeal passageways of the human body in supine position, and wherein the blade is provided with means for indirect visualization of the glottis without disturbing the normal position of the head of the body in supine position.

9 Claims, 4 Drawing Figures

LARYNGOSCOPE

The present invention is directed to a laryngoscope for visualizing the laryngeal area of the human body and, more particularly, to an improved laryngoscope blade for use in indirect visualization of the glottis to facilitate oral or transnasal intubation of the trachea.

Laryngoscopes are widely known and used in the medical field to facilitate endotracheal intubation of a patient during surgery to provide a positive air passageway for the administration of anesthesia and/or for the mechanical ventilation of the lungs of the patient. In the human anatomy, the epiglottis normally overlies the glottis opening into the larynx to prevent the passage of food into the trachea during eating; therefore, in endotracheal intubation, it is necessary to displace the epiglottis from the glottal opening to permit the air tube to be inserted into the trachea.

Various laryngoscope constructions are known. The more widely used laryngoscopes consist of an elongate, rigid metal blade which is supportably attached to a handle and is inserted through the mouth of the patient into the pharyngeal area to displace the tongue and epiglottis and permit direct visualization of the glottis through the mouth opening. Such laryngoscopes are generally provided with a light source which is directed along the blade to illuminate the area beyond the distal end of the blade. Two general types of rigid blade constructions are the straight, or so called "Miller blade," and the slightly curved, or so called "MacIntosh blade." Curved laryngoscope blade constructions having the light means to facilitate illumination of the areas of observation are described in U.S. Pat. Nos. 3,598,113; 3,643,654; 3,766,909, and 3,771,514.

The standard method for performing intubation of the trachea during surgery with rigid laryngoscope blades of the straight or slightly curved type is to place the patient in supine position, tilt the head backwards as far as possible, and distend the lower jaw to widely open the mouth. The rigid blade is then inserted through the mouth into the throat passageway to displace the tongue and epiglottis and expose the glottis of the patient. The larynx is then viewed through the mouth opening from an observation position just above and beyond the head of the patient by sighting generally along the axis of the blade. The endotracheal tube is inserted, either orally or transnasally, and passed alongside the blade into the glottis.

The use of such blades for visualizing the glottis can present many problems and disadvantages in certain applications. Since the head must be forceably tilted and the neck extended with the mouth widely opened to permit visualization of the glottis, such body manipulations can further complicate and severely injure patients having spinal, neck or facial injuries, such as fractures and the like. In addition, such blades, frequently contact and are pivoted about the edge of the upper teeth during use and breakage or injury of the teeth often results therefrom. Such blades are also difficult, if not impossible, to employ in many patients having physical malformations of the jaw or tumors of the throat which would preclude direct visualization of the glottis.

Surgical instruments having means for indirect illumination and visualization of the pharyngeal areas of the body are known. U.S. Pat. Nos. 3,776,222 and 3,913,568 disclose devices for endotracheal intubation which comprise flexible or articulatable tubular probes having internal fiber optics for lighting and viewing the internal areas of the body. As disclosed in said patents, the probes carry a slidably removeable endotracheal tube around their outer surfaces and the probe is directly inserted into the trachea to position the tube. Such devices obviously require the use of relatively large diameter endotracheal tubes in order to be carried on the tubular probe, and their use necessarily is limited to patients with sufficiently large airway passages to accommodate the combined size of the probe and endotracheal tube. Additionally, due to the flexible nature of the probes, it is difficult to manipulate the probe to displace the tongue and epiglottis to permit direct insertion of the tube into the trachea.

U.S. Pat. No. 3,677,262 discloses a surgical instrument employing internal fiber optics in a rigid tube which carries an endotracheal tube on its outer surface. The instrument not only requires the use of large endotracheal tubes with the limitations mentioned above, but its generally straight configuration requires hyperextension of the head and neck during use, as with the Miller and MacIntosh rigid, blade-type constructions described above.

It is therefore an object of the present invention to provide an improved laryngoscope blade construction which overcomes the problems which have been experienced with laryngoscope constructions of the prior art.

It is a further object to provide an improved laryngoscope blade shape which may be utilized for intubation of a patient without having to contact or displace the normal body position and bone structure of a patient during examination.

In its broad aspects, the present invention is directed to a rigid laryngoscope blade construction which is anatomically shaped to conform to the normal longitudinal axis of the human mouth and throat passageway from the opening to the oral cavity to the epiglottis. The blade is further provided with means to permit indirect illumination and visualization of the laryngeal areas of the body so that the blade may be utilized for intubation of the trachea without disturbing the normal position of the head of a patient in supine position and without contacting the bone structure during use.

The above as well as other objects of the present invention will become more apparent, and the invention will be better understood from the following detailed description of a preferred embodiment of the invention, when taken with the accompanying drawings, in which FIG. 1 is a perspective view of a laryngoscope blade of the present invention;

Figure 1:
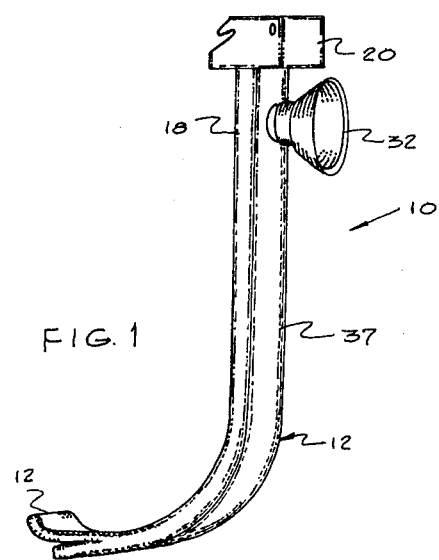
Figure 3:
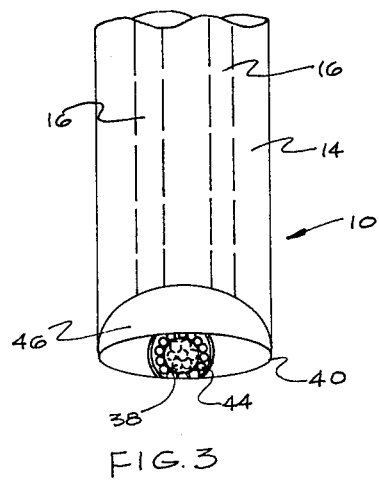
FIG. 3 is a broken-away, left end view of the distal end and lower anterior surface of the blade as shown in FIG. 2.

Referring more specifically to the drawings, and as seen in FIG. 1, the laryngoscope 10 of the present invention comprises a thin, rigid blade 12 of anatomically curved configuration which is constructed of a suitable high strength material, such as metal or plastic. As seen in FIG. 3, the anterior, or inner, curved surface 14 of the blade is relatively wide in transverse direction, and the blade may be slightly concave from side to side, or provided with longitudinal grooves or ribs 16 (shown in broken lines) to facilitate frictional retention of the tongue thereon during use, as will be explained.

Figure 2:
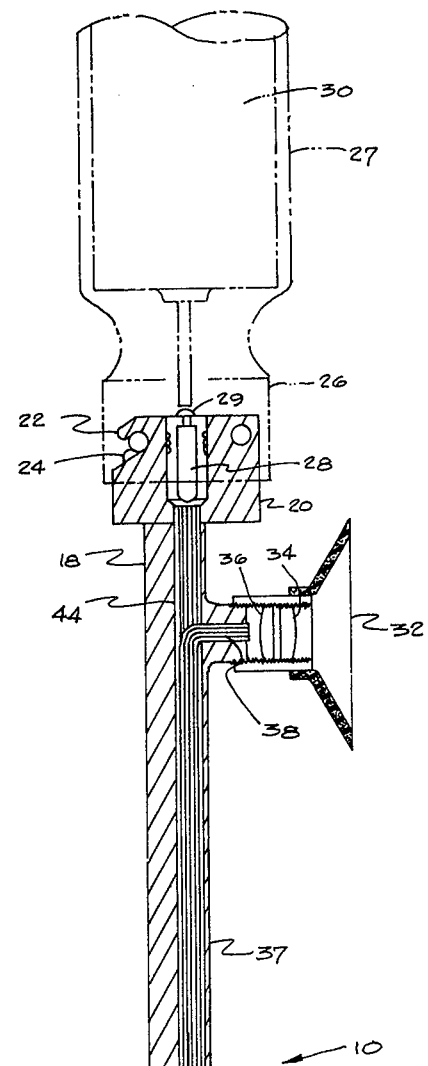
FIG. 2 is an enlarged side longitudinal section view of the blade shown in FIG. 1.
Figure 2:
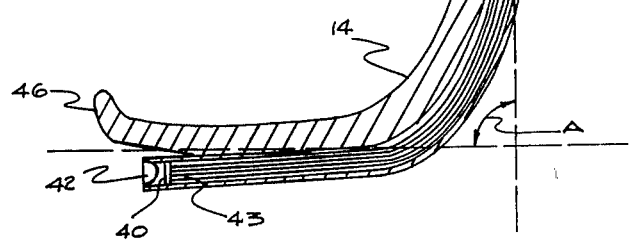
Figure 4:
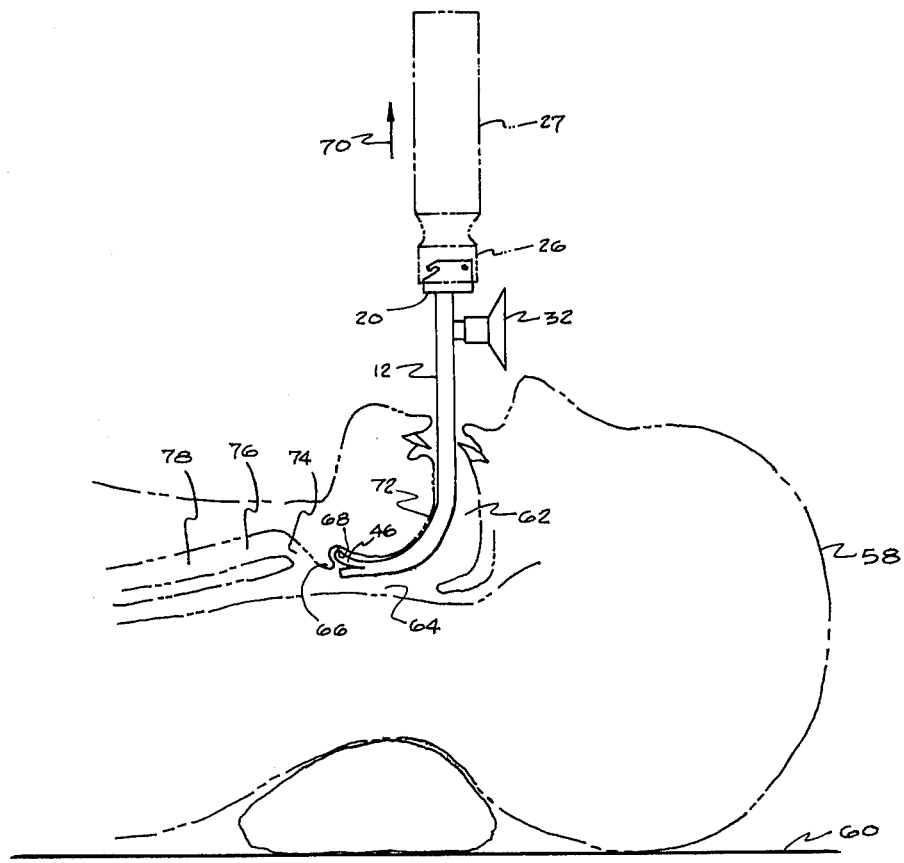
FIG. 4 is a side elevation view showing the laryngoscope blade positioned for intubation of a patient in supine position.

The proximal end 18 of the blade is provided with a connection member 20 having a projecting finger-like element 22 defining a slot or groove containing a spring-loaded detent 24 to provide for removable attachment of the blade to a conventional connection member 26 on the end of a conventional laryngoscope battery handle 27 (shown in phantom lines in FIGS. 2 and 4). Connection member 20 contains a light bulb 28 (FIG. 2) which is electrically connected through a contact 29 and suitable electrical conductor means to the battery power supply 30 in the handle when the blade is attached thereto.

As best seen in FIG. 2, an eyepiece 32 containing lens members 34, 36 is attached to and extends outwardly from the posterior, or outer, curved surface 37 of the blade 12 at the proximal end portion thereof. Lens members 34, 36 optically communicate with the end of a coherent bundle 38 of optical fibers. The bundle 38 extends along the longitudinal axis of the blade adjacent the posterior surface thereof to a lower distal tip portion 40 of the blade and communicates with an opening 42 containing a lens 43 therein to permit indirect visualization of the area beyond the distal end of the blade through eyepiece 32. Surrounding the optical fiber bundle 38 is a second bundle or group of optical fibers 44 which extends from the light bulb 28 to the distal tip opening 42 to transmit light into the area beyond the distal end of the blade. The arrangement of the two fiber optic bundles at the distal tip of the blade is best seen in FIG. 3.

As seen in FIGS. 2 and 3, the distal end of the blade also is provided with a second tip portion 46 which projects slightly upwardly and inwardly of the main longitudinal axis of the blade and the fiber optic opening 42. The tip 46 is designed and positioned to facilitate lifting of the epiglottis during use of the blade, as will be explained.

FIG. 4 shows the use and position of the blade of the present invention in visualizing the glottis and larynx of a patient. The head, upper torso, and internal oral, pharyngeal, and laryngeal passageways of a human body are shown in phantom lines for better illustration. With the patient in supine position and with the head 58 resting normally on the upper surface 60 of an operating table, the blade 12 is inserted into the mouth by the anesthesiologist normally stationed at the end of the operating table to the right and beyond the head of the patient, as seen in FIG. 4. Due to the thin anterior-posterior dimension and the anatomically curved shape of the blade, it is easily passed between the teeth and through the oral and pharyngeal passageways 62, 64 to a point adjacent the epiglottis 66. As the pharyngeal and laryngeal areas are indirectly viewed through the eyepiece 32, the upwardly turned tip 46 of the blade is inserted into the velecula 68. By merely raising laryngoscope handle 27 a short distance in the vertical direction, as indicated by arrow 70, the tongue 72 is lifted and retained on the blade and the epiglottis 66 raised to expose the glottis 74 and permit visualization of the glottis and larynx 76 through the eyepiece. In the event the epiglottis is enlarged or otherwise malformed in such a way that it is not readily displaced from the glottis with the tip inserted into the velecula, the tip may just as readily be placed directly beneath the epiglottis itself and the blade raised vertically to expose the glottis. An endotracheal tube may then be passed either transnasally or orally alongside the blade and inserted through the glottis into the trachea 78. The blade is withdrawn from the mouth to complete the intubation procedure.

As seen in FIGS. 2 and 4, battery handle 27 is attached to the blade to lie along an extension of the longitudinal axis of the blade, rather than at a right angle thereto. By so locating the handle, the area above the lower jaw and chest of the patient is free from obstruction by the laryngoscope and is thus available for other surgical procedures during intubation.

As illustrated in FIG. 4, in the normal anatomy of a human body in supine position, the longitudinal axis of the oral passageway and the longitudinal axis of the pharyngeal passageway describe an acute angle of about 90°; therefore, it is desirable that the curvature of the blade be such that the longitudinal axis of the blade at the distal end portion forms an angle between about 80° to 100° with the longitudinal axis at the proximal end portion, as illustrated by the angle A in FIG. 2. The exact length of the blade, and particularly the proximal end portion thereof, may be varied so that the eyepiece 32 is located at a desired elevation above the head of the patient to permit easy viewing of the glottis when the distal tip is positioned to displace the epiglottis. Shorter length blades may also be employed in intubation of small children and infants.

From the foregoing description of the construction and use of the invention, it can be seen that by providing a rigid laryngoscope blade of anatomically curved shape with the distinctive features described, the blade can be readily employed to permit exposure and visualization of the glottis without disturbing the normal position of the head, neck, or body of a patient in supine position.

That which is claimed is:

1. An improved laryngoscope for use in indirect visualization of the glottis without disturbing the normal position of the head of a human in supine position, comprising a rigid elongate blade having a width greater than its thickness and a longitudinal axis between proximal and distal end portions generally conforming in curvature to the longitudinal curvature of the passageway from the entrance of the oral cavity to the epiglottis of the normal human anatomy, the longitudinal axis of the blade at the distal end portion defining an acute angle of between 80° and 100° with the longitudinal axis of the blade at the proximal end portion, and means extending along the blade for transmitting light into an area beyond the distal end of the blade and for transmitting visual images from said area to a position adjacent the proximal end portion of the blade.

2. A laryngoscope as defined in claim 1 wherein said blade includes connection means on said proximal end portion, and handle means removably attached to said connection means and extending generally along an extension of the longitudinal axis of said blade at said proximal end portion.

3. A laryngoscope as defined in claim 1 including eyepiece means extending outwardly from the proximal end portion of the blade and communicating with said visual image transmitting means for visualizing said area beyond the distal end portion of the blade.

4. A laryngoscope as defined in claim 3 wherein said blade includes an opening in the distal end portion, and wherein said transmitting means comprises an elongate bundle of optical fibers within said blade extending from said eyepiece means to said opening for transmitting visual images from said opening to said eyepiece means.

5. A laryngoscope as defined in claim 4 wherein said blade includes light means at said proximal end portion, and said transmitting means includes elongate optical fibers within said blade extending from said light means to said distal end opening for transmitting light into said area beyond the distal end of the blade.

6. A laryngoscope as defined in claim 1 wherein said blade includes a first distal tip portion having an opening therein lying substantially on the longitudinal axis of the distal portion of the blade for transmitting light into and receiving visual images from said area beyond the distal end of the blade, and a second distal tip portion extending inwardly of the curvature of said blade from said longitudinal axis for engaging the vellecula or epiglottis of the human body.

7. A laryngoscope as defined in claim 1 wherein the inner curved surface of said blade is relatively wide in transverse dimension and includes means for frictionally retaining the tongue thereon during displacement thereby.

8. An elongate rigid laryngoscope blade for use in visualization of the glottis, said blade having an longitudinally curved configuration between proximal and distal ends thereof conforming to the longitudinal axial curvature of the normal human oral and pharyngeal passageway from the mouth opening to the epiglottis, means on the proximal end portion of said blade for attachment to a handle, eyepiece means on the proximal end portion of said blade extending outwardly from the outer longitudinally curved surface of the blade at a generally right angle thereto, light means on the proximal end portion of said blade, an opening in the distal end portion of said blade, and means on the interior of said blade extending from said opening to said light means and said eyepiece means for transmitting light from said light means through said opening into an area beyond the distal end of said blade and for transmitting visual images from said area to said eyepiece means to permit indirect visualization of said area through said eyepiece means.

9. A blade as defined in claim 8 wherein the longitudinal axis of the proximal end portion of the blade describes an angle of about 80° to 100° with the longitudinal axis of the distal end portion of the blade, and wherein the blade includes a distal tip portion extending radially inwardly of the longitudinal axis of the distal end portion of the blade to permit insertion of the tip into the vellecula.

* * * * *